United States Patent [19]

Allmendinger et al.

[11] Patent Number: 5,003,074
[45] Date of Patent: Mar. 26, 1991

[54] N-FLUORINATED SULFONAMIDES

[75] Inventors: Thomas Allmendinger, Steinen, Fed. Rep. of Germany; Edmond Differding, Binningen; Robert W. Lang, Pratteln, both of Switzerland

[73] Assignee: Ciba-Geigy Corporation, Ardsley, N.Y.

[21] Appl. No.: 250,291

[22] Filed: Sep. 28, 1988

[30] Foreign Application Priority Data

Oct. 9, 1987 [CH] Switzerland .................. 3956/87

[51] Int. Cl.$^5$ .................. C07D 275/02; C07D 275/06
[52] U.S. Cl. ........................ 548/206; 548/207; 548/208; 548/214; 548/110; 540/467; 540/468; 540/544; 540/552; 544/3; 544/47; 544/49
[58] Field of Search ............... 548/208, 110, 207, 206, 548/214; 564/114; 546/114; 540/468, 552, 467, 544; 544/47, 49, 3

[56] References Cited

U.S. PATENT DOCUMENTS 4,479,901 10/1984 Barnette .................. 260/239

FOREIGN PATENT DOCUMENTS 0211578 2/1987 European Pat. Off. .

OTHER PUBLICATIONS

J. Am. Chem. Soc. 1986, 108, 2445–2447.
J. Org. Chem. 1982, 47, 3966–3969.

Primary Examiner—Mukund J. Shah
Assistant Examiner—Philip I. Datlow
Attorney, Agent, or Firm—Stephen V. O'Brien; Michael W. Glynn

[57] ABSTRACT

Compounds of formula I

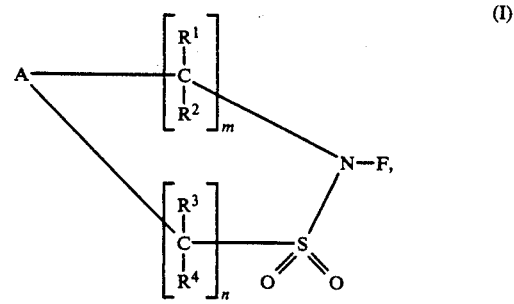

wherein $R^1$, $R^2$, $R^3$ and $R^4$ are H, alkyl or aryl, m and n are 0 or 1, and A is a divalent organic radical which, with $(CR^1R^2)_m NF-SO_2(CR^3R^4)_n$ groups, forms a 5- to 8-membered ring, are admirably suitable fluorinating agents for fluorinating carbon atoms, especially as stereospecific fluorinating agents, when the compounds contain a chiral carbon atom and are in optically active form. The compounds of formula I are prepared by reacting the corresponding silated sulfonamides, wherein the NF group is replaced by an $N-SiR^7R^8R^9$ group and $R^7$, $R^8$ $R^9$ are each independently $C_1-C_{12}$alkyl, cyclopentyl, cyclohexyl, benzyl or phenyl, with a fluorinating agent.

17 Claims, No Drawings

N-FLUORINATED SULFONAMIDES

The present invention relates to cyclic N-fluorinated sulfonamides, to cyclic N-silylated sulfonamides as intermediates, to a process for their preparation by direct fluorination, and to the use thereof for the fluorination of carbon compounds.

N-Substituted N-fluoroarylsulfonamides which are used for the fluorination of carbanions are disclosed in U.S. Pat. No. 4,479,901. Even when carried out with highly dilute mixtures of $F_2/N_2$ and at low reaction temperatures, the direct fluorination of corresponding N-H-sulfonamides without HF neutralisers results, as a consequence of HF formation, in side reactions that are generally reflected in very low yields. The stereospecific synthesis of alkenyl fluorides by reacting alkenyl lithium with N-tert-butyl-N-fluorophenylsulfonamide is described in J. Am. Chem. Soc., Vol. 108, No. 9, pp. 2445-2447 (1986).

European patent application No. A-0 211 578 discloses perfluorinated N-fluorinated bis(sulfonamides) which can be used for the electrophilic fluorination of the ring carbon atoms of aromatic compounds and for fluorinating carbanions. These compounds are somewhat unstable and even their preparation has to be effected at very low temperature and requires special precautionary measures.

It is an object of the present invention to provide compounds of formula I

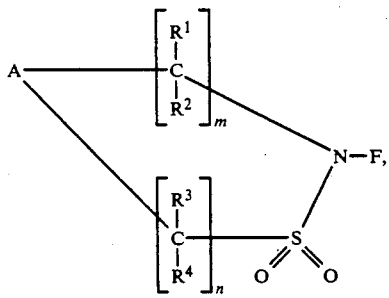

wherein $R^1$, $R^2$, $R^3$ and $R^4$ are each independently H, linear or branched $C_1$–$C_{18}$alkyl or $C_6$–$C_{10}$aryl, each unsubstituted, or alkyl is substituted by halogen, $C_6$–$C_{10}$aryl or $C_6$–$C_{10}$aryloxy, $C_1$–$C_6$alkoxy or secondary amino, and aryl is substituted by $C_1$–$C_{12}$alkyl, $C_1$–$C_{12}$haloalkyl or $C_1$–$C_{12}$alkoxy, halogen, phenyl, phenoxy or secondary amino, m and n are each independently of the other 0 or 1, and A is a divalent organic radical which, together with the $\text{+(CR}^1\text{R}^2\text{)}_{\overline{m}}\text{NF—SO}_2\text{(CR}^3\text{R}^4\text{)}_{\overline{n}}$ group, forms a 5- to 8-membered ring, and the radical A is selected from the group consisting of (a) $C_1$–$C_6$alkylene, $C_2$–$C_6$alkenylene, $C_4$–$C_6$alkdienylene, $C_6$alktrienylene, $C_5$–$C_8$cycloalkylene, $C_5$–$C_8$cycloalkenylene, $C_5$–$C_8$cycloalkdienylene or $C_7$–$C_8$cycloalktrienylene, each of which radicals may be fused to a carbocyclic or heterocyclic ring, or the cycloaliphatic radicals may be bridged with a $\text{+(CR}^5\text{R}^6\text{)}_{\overline{x}}$ group, wherein $R^5$ and $R^6$ are each independently of the other H or $C_1$–$C_4$alkyl and x is 1 or 2;

(b) $C_6$–$C_{14}$arlyene or heteroarylene containing 5 or 6 ring carbon atoms and 1 or 2 hetero atoms selected from O, S and tertiary N, and the ring A is unsubstituted or substituted by one or more of $C_1$–$C_6$alkyl or $C_1$–$C_6$alkoxy, secondary amino, phenyl, phenoxy, Cl and Br, and the radical A, as cyclic radical, is also substituted by F.

$R^1$, $R^2$, $R^3$ and $R^4$ can be linear or branched alkyl of preferably 1 to 12, more particularly 1 to 6 and, most preferably, 1 to 4, carbon atoms. Examples of such alkyl groups are methyl, ethyl and the isomers of propyl, butyl, pentyl, hexyl, heptyl, octyl, nonyl, decyl, undecyl, dodecyl, tridecyl, tetradecyl, pentadecyl, hexadecyl, heptadecyl and octadecyl. Preferred alkyl groups are hexyl, pentyl, n-butyl, isobutyl and tert-butyl, n-propyl and isopropyl, ethyl and methyl. Methyl and ethyl are especially preferred.

$R^1$, $R^2$, $R^3$ and $R^4$ may be $C_6$–$C_{10}$aryl, preferably napthyl and, most preferably, phenyl.

$R^1$, $R^2$, $R^3$ and $R^4$ as alkyl may be substituted by halogen, preferably Br, Cl and F; $C_6$–$C_{10}$aryl or $C_6$–$C_{10}$aryloxy, for example phenyl or phenoxy; $C_1$–$C_6$alkoxy, for example methoxy, ethoxy, n-propoxy, isopropoxy, n-butoxy, isobutoxy or tert-butoxy; secondary amino, for example $(C_1-C_6\text{alkyl})_2N$—, wherein alkyl is preferably methyl, ethyl, propyl or butyl. $R^1$, $R^2$, $R^3$ and $R^4$ as aryl may be substituted by $C_1$–$C_{12}$alkyl, preferably by $C_1$–$C_6$alkyl, and, most preferably, by $C_1$–$C_4$alkyl, for example butyl, propyl and, preferably, methyl and ethyl; $C_1$–$C_{12}$haloalkyl, preferably $C_1$–$C_4$haloalkyl, for example fluoromethyl or chloromethyl, difluoromethyl or dichloromethyl and trifluoromethyl or trichloromethyl; $C_1$–$C_4$alkoxy, for example methoxy and ethoxy; halogen, for example Br, Cl and F; phenyl; phenoxy; or, as previously mentioned for alkyl, by secondary amino. $R^1$, $R^2$, $R^3$ and $R^4$ are preferably unsubstituted.

In a preferred subgroup $R^1$, $R^2$, $R^3$ and $R^4$ are each independently H or unsubstituted or substituted $C_1$–$C_6$alkyl.

In formula I, m and n are preferably 1, or m is 0 and n is 1, or m is 1 and n is 0.

In a preferred subgroup, A together with the $\text{+(CR}^1\text{R}^2\text{)}_{\overline{m}}\text{NF—SO}_2\text{(CR}^3\text{R}^4\text{)}_{\overline{n}}$ group is a 6-membered and, preferably, a 5-membered ring, wherein preferably m is 0 and n is 1, or n is 0 and m is 1. In a particularly preferred subgroup, A is a cycloaliphatic radical as defined previously, to which the —NF—SO₂—CR³R⁴— group is attached in 1,2-position, or is an arylene or heteroarylene radical to which the —CR¹R²—NF—SO₂— group is attached in 1,2-position.

The radical A may be selected from the following groups, the cyclic radicals being preferably attached in α,β-position to the $\text{+(CR}^1\text{R}^2\text{)}_{\overline{m}}\text{NF—SO}_2\text{(CR}^3\text{R}^4\text{)}_{\overline{n}}$ group:

1. $C_1$–$C_6$alkylene, preferably $C_1$–$C_4$alkylene and, most preferably, alkylene of 1 or 2 carbon atoms, for example 1,6-hexylene, 1,5-pentylene, 1,4-butylene, 1,3-propylene and, in particular, ethylene or methylene;

2. $C_2$–$C_6$alkenylene, preferably $C_2$–$C_4$alkenylene, for example hex-1-en-1,6-ylene, hex-3-en-1,6-ylene, pent-2-en-1,5-ylene, but-1-en-1,4-ylene, but-2-en-1,4-ylene, but-3-en-1,4-ylene or but-4-en-1,4-ylene, prop-1-en-1,3-ylene or prop-3-en-1,3-ylene and, preferably, ethenylene;

3. $C_4$–$C_6$alkdienylene, for example buta-1,3-dien-1,4-ylene, penta-1,3-dien-1,5-ylene or penta-1,4-dien-1,5-ylene, penta-2,4-dien-1,5-ylene, hexa-1,3-dien-1,6-ylene, hexa-1,4-dien-1,6-ylene or hexa-1,5-dien-1,6-ylene, hexa-2,4-dien-1,6-ylene or hexa-2,5-dien-1,6-ylene, and hexa-3,5-dien-1,6-ylene;

4. $C_6$alktrienylene, for example hexa-1,3,5-trien-1,6-ylene;

5. $C_5$–$C_6$cycloalkylene, for example cyclopentylene, cyclohexylene, cycloheptylene and cyclooctylene, with cyclopentylene and cyclohexyl being especially preferred;

6. $C_5$-$C_8$cycloalkenylene, preferably cycloalkenylene of 5 or 6 carbon atoms, for example cyclooctenylene, cycloheptenylene, cyclohex-1-, -2-, -3-, -4-, -5- or -6-en-1,2-ylene, cyclopent-1-, -2-, -3-, -4- or -5-en-1,2-ylene;

7. $C_5$-$C_8$cycloalkdienylene, preferably cycloalkdienylene of 5 or 6 carbon atoms, for example cyclooctadienylene, cycloheptadienylene, cyclohexa-1,3-, -1,4-, -1,5-, -2,4-, -2,5-, -2,6-, -3,5- or -3,6-dien-1,2-ylene, cyclopenta-1,3-, -1,4-, -2,4-, -2,5- or -3,5-dien-1,2-ylene;

8. $C_7$cycloalktrienylene or $C_8$cycloalktrienylene, for example cyclohepta-1,3,5-, -2,4,6- or -3,5,7-trien-1,2-ylene, cycloocta-1,3,5-, -2,4,6-, -3,5,7-, -4,6,8-, -1,4,6-, -1,5,7- or -2,5,7-trien-1,2-ylene;

9. $C_6$-$C_{14}$arylene, preferably $C_6$-$C_{10}$arylene, in particular 1,2- or 2,3-naphthylene or 1,2-phenylene;

10. Heteroarylene containing 5 or 6 ring atoms and one or two hetero atoms, preferably one hetero atom, selected from O, S and tertiary nitrogen, which tertiary nitrogen atom may be the group =N— or a substituted, for example a $C_1$-$C_4$alkyl-substituted, secondary nitrogen atom; and heteroaryl from which the radical A may be derived is, for example, pyridine, pyrimidine, thiophene, furan, pyran, N-substitituted pyrrole or indole, benzofuran, benzothiophene, quinoline and isoquinoline;

11. The alkylene, alkenylene, alkdienylene, alktrienylene, cycloalkylene, cycloalkenylene, cycloalkdienylene, and cycloalktrienylene radicals can be fused with a carbocyclic or heterocyclic ring, which carbocyclic ring preferably contains 5 or 6 carbon atoms and may be a cycloaliphatic or aromatic ring, and which hetrocyclic ring contains two hetero atoms, preferably one hetero atom, selected from the group O, S and tertiary N and contains 5 or 6 ring atoms and may be a heterocycloaliphatic or heteroaromatic radical. The tertiary nitrogen atom can be the group =N— or a substituted, for example $C_1$-$C_4$alkyl-substituted, secondary nitrogen atom. Examples of such carbocyclic and heterocyclic rings are cyclopentane, cyclohexane, cyclopentene, cyclohexene, cyclopentadiene, cyclohexadiene, benzene, pyridine, thiophene, furan, N-substituted pyrrole, dihydrofuran or tetrahydrofuran, or dihydrothiophene or tetrahydrothiophene, N-substituted piperidine, morpholine, pyrrolidine or pyrroline;

12. A cycloaliphatic radical A can be bridged with a group $-(CR^5R^6)_x$, wherein $R^5$ and $R^6$ are each independently of the other preferably H, $CH_3$ or $C_2H_5$, and the bridging group is preferably methylene, ethylidene, 1,1- or 2,2-propylidene, ethylene or methylethylene. Exemplary of such bridged cycloaliphatic rings which contain preferably 6 to 14, most preferably 6 to 10, carbon atoms and from which the radical A may be derived, are: bicyclo[2.2.0]hexane, bicyclo[2.2.1] heptane, bicyclo[2.2.2]octane, bicyclo[3.1.1]heptane, bicyclo[3.2.1]octane, bicyclo[3.3.0]octane, bicyclo[3.4.0]nonane, bicyclo[3.3.1]nonane, bicyclo[2.2.1]-6,7,7-trimethylheptane, and bicyclo[2.2.2]-7-methyloctane.

The radical A can be unsubstituted or can carry one or more, preferably one to three, substituents. Suitable substituents are $C_1$-$C_6$alkyl, for example methyl, ethyl, n-propyl or isopropyl, n-butyl, isobutyl or tert-butyl, pentyl, hexyl; $C_1$-$C_6$alkoxy, preferably methoxy or ethoxy; secondary amino, for example ($C_1$-$C_6$alkyl)$_2$N—, wherein alkyl is preferably methyl, ethyl, propyl or butyl; phenyl; phenoxy; Cl, Br and, if the radical R is a cyclic radical, also F.

A preferred group of compounds of formula I comprises those wherein m and n are 1 and A is unsubstituted or substituted alkylene of 1 or 2 carbon atoms which can be fused with a carbocyclic ring.

Another group of preferred compounds comprises those wherein m is 0 and n is 1, or m is 1 and n is 0, and A is unsubstituted or substituted alkenylene of 2 to 3 carbon atoms, or cycloalkylene, cycloalkenylene or cycloalkdienylene, each of 5 or 6 carbon atoms, and each of which radicals may be fused with a carbocyclic ring or the cyclic radicals may be bridged with a $-(CR^5R^6)_x$ group, wherein $R^5$ and $R^6$ are each independently of the other $C_1$-$C_4$alkyl or H, and x is 1 or 2. The carbocyclic ring is in these groups preferably a naphthalene or benzene ring.

Also preferred are those compounds of formula I wherein n is 0 and m is 1 or m is 0 and n is 1, and the radical A is unsubstituted or substituted 1,2-naphthylene, 1,2-phenylene or 2,3-pyridylene.

Surprisingly, it has been found that the compounds of this invention are stereoselective and, in the fluorination of olefinic carbanions, form only the E or Z isomer in high yield. If, in addition, the compounds of this invention are chiral, and in such cases are used in the form of a single optically active stereoisomer, then, surprisingly, the fluorination of secondary and tertiary aliphatic carbanions results in some cases in very high optical yields of only one stereoisomer.

Hence a preferred subgroup of compounds of formula I comprises those compounds in which the carbon atoms of the $-(CR^1R^2)-$ group and/or $-(CR^3R^4)-$ group are chiral, and/or the radical A contains at least one chiral carbon atom, in the form of their racemates and/or individual stereoisomers.

It has also been found that the optical induction is especially high when the chiral carbon atom is close to the NF group in formula I. More preferred are therefore those compounds in which the chiral carbon atoms in formula I are in α- or β-orientation to the NF group.

Another group of preferred compounds of formula I comprises those wherein m is 1 and n is 0, $R^1$ and $R^2$ are as defined in claim 1 and A is unsubstituted or substituted 1,2-phenylene, in particular those chiral compounds in which $R^1$ and $R^2$ are different radicals, in the form of their racemates and stereoismers. A particularly preferred compound is 3-deoxy-3,3-dimethyl-N-fluorosaccharin.

Further, those chiral compounds of formula I are preferred wherein m is 0 and n is 1, $R^3$ and $R^4$ are each H and A is unsubstituted or substituted $C_5$-$C_6$cycloalkylene which contains at least one chiral carbon atom and which can be bridged preferably with methylene, ethylidene, 1,1- or 2,2-propylidene or ethylene, in the form of their racemates or stereoisomers. Among these compounds, those compounds are especially preferred in which A is cyclohexylene which is unsubstituted or substituted in α-position to the NF group by $C_1$-$C_4$alkyl or phenyl, and which can be bridged with methylene, ethylidene, 1,1- or 2,2-propylidene or ethylene.

Particularly preferred are N-fluorocamphor sultams of formula III

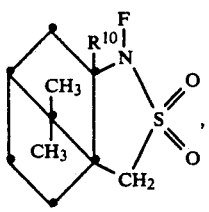

(III)

wherein $R^{10}$ is H, linear or branched $C_1$–$C_6$alkyl or phenyl, in the form of their racemates or stereoisomers.

An especially individual compound is N-fluorocamphor sultam of formula

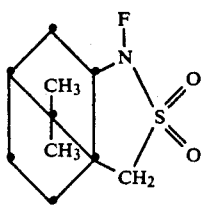

in the form of its racemate or of the individual stereoisomers.

The compounds of formula I are mainly crystalline compounds that are generally stable and easy to handle. In the course of time, elimination of HF may become noticeable in compounds of formula I which in α-position to the NF group contain a hydrogen atom, so that it is advisable to use them soon after their preparation.

The compounds of formula I can be obtained by processes known per se by direct fluorination of compounds of formula IV

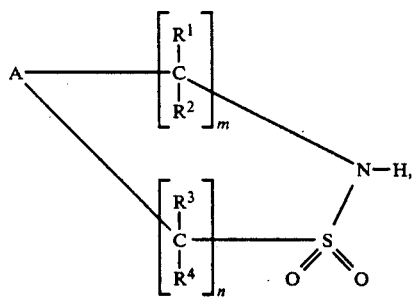

(IV)

wherein $R^1$ to $R^4$, m, n and A have the meanings previously assigned to them. A corresponding process without the use of a HF neutraliser is disclosed in U.S. Pat. No. 4,479,901.

It is particularly convenient to carry out the direct fluorination in the presence of a HF neutraliser. Examples of suitable HF neutralisers are molecular sieves or an alkali metal fluoride such as LiF, NaF, KF or CsF, or tertiary amines.

An electrofluorination is disclosed in European patent application No. A-0 211 578.

Some of the compounds of formula IV are known and commercially available, or they can be prepared by known methods. One process is described, for example, in J. Chem. Soc., page 1339 (1952), and another in Helv. chim. Acta, Vol. 67, pp. 1397.1401 (1984). The group $R^{10}$ in the significance of $C_1$–$C_6$alkyl and phenyl can be introduced by alkylating and phenylating reagents respectively.

The known processes for fluorinating N-H-sulfonamides have the drawback that side reactions diminish the yield. Surprisingly, it has been found that the direct fluorination in virtually quantitative yield is possible in short reaction times by carrying out the reaction in the presence of a HF neutraliser or by using N-silylated sultams as starting materials.

The present invention further relates to a process for the preparation of compounds of formula I, which comprises reacting a compound of formula II

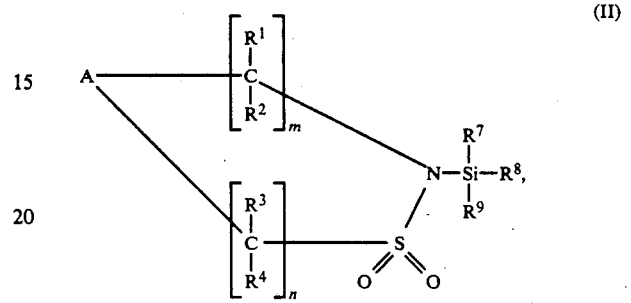

(II)

wherein A, $R^1$, $R^2$, $R^3$, $R^4$, m and n have the meanings previously assigned to them, and $R^7$, $R^8$ and $R^9$ are each independently linear or branched $C_1$–$C_{12}$alkyl, cyclopentyl, cyclohexyl, benzyl or phenyl, with a fluorinating agent.

Suitable fluorinating agents are, for example, $F_2$, $CF_3OF$ or $CH_3COOF$.

The compounds of formula II likewise constitute an object of the invention. They can be obtained in simple manner by known methods by silylating compounds of formula IV. Such methods are described, for example, in E. Colvin, Silicon in Organic Synthesis, Butterworth, London (1981), or in the thesis by Hans Baumann, No. 7932, ETH Zürich (1985). The same preferences apply to $R^1$ to $R^4$, A, m and n as previously described for the compounds of formula I. $R^7$, $R^8$ and $R^9$ may each independently be linear or branched alkyl of preferably 1 to 6, most preferably, 1 to 4, carbon atoms. The particularly preferred meaning of $R^7$, $R^8$ and $R^9$ is methyl.

The process can be carried out in the presence of a solvent. Examples of suitable solvents are chlorinated and/or fluorinated hydrocarbons or nitriles, for example methylene chloride, chloroform, carbon tetrachloride, 1,2-dichloroethane, 1,1,1-trichloroethane, 1,1,2,2-tetrachloroethane, fluorotrichloromethane, 1,1,1-trifluoro-2,2,2-trichloroethane, hexafluorobenzene and acetonitrile.

The direct fluorination is conveniently carried out with a mixture of inert gas and fluorine. Suitable inert gases are, for example, rare gases such as helium, neon and argon, or nitrogen. The proportion of fluorine in the mixture can be from 0.1 to 99.9, preferably 0.5 to 50 and, most preferably, 1 to 20, percent by volume.

The reaction temperature can be in the range from −100° to +80° C., preferably from −80° to +20° C. and, most preferably, from −50° to +20° C.

It is expedient to carry out the reaction excluding oxygen and moisture.

The desired compounds can be isolated in conventional manner, for example by evaporation of the solvent and subsequent distillation, sublimation or crystallisation. The product so obtained can be additionally purified, for example by recrystallisation or by chromatographic methods.

The compounds of formula I are excellent fluorinating agents of carbon compounds and hence valuable reagents for the preparation of, for example, fluorinated biologically active compounds. Especially advantageous is the possibility of stereoslective fluorination, as specific stereoiosmers are known to have a greater biological activity than their antipodes.

The fluorination of carbon compounds is disclosed, for example, in U.S. Pat. No. 4,479,901, European patent application No. A-0 211 578, and J. Am. Chem. Soc., Vol. 108, pp. 2445-2447. Suitable carbon compounds are, for example, carbanions. Suitable carbanions may be represented, for example, by the general formula $C^-{}_zM^{Y+}X_{y-z}$, wherein C is the organic radical of a carbanion, M is a metal or semimetal, X is halogen, preferably Cl, z is an integer from 1 to 4, and y is the valency of the metal. Examples of M are Li, Na, K, Mg, Cd, Zn, Al, Ti, Zr, Si. M may also be quaternary ammonium. In addition, carbanions stabilised with, for example, N, S, p or Se (ylides) can also be fluorinated with the compounds of this invention.

The fluorination is normally carried out in the presence of a solvent, conveniently a polar aprotic solvent such as an ether (diethyl ether, dibutyl ether, tetrahydrofuran, dioxane, ethylene glycol dimethyl ether) and in the temperature range from, for example, $-100°$ C. to $+100°$ C., preferably from $-100°$ C. to $+50°$ C. and, most preferably, from $-80°$ C. to $+20°$ C.

The invention further relates to the use of the compounds of formula I for fluorinating carbon compounds, especially compounds of formula I in the form of an optically active stereoisomer of a chiral compound for stereoselective fluorination of carbon compounds.

The following Examples illustrate the invention in more detail.

(A) PREPARATORY EXAMPLES

EXAMPLE 1

N-Trimethylsilyl-3-deoxy-3,3-dimethylsaccharin 100 mmol of 3-deoxy-3,3-dimethylsaccharin [prepared in accordance with the procedure described in J. Chem. Soc., p. 1339 (1952)] are heated for 20 hours at reflux in an argon atmosphere and in an excess of hexamethyl disilazane in accordance with Hans Baumann, Thesis No. 7932, ETH Zürich. The reaction mixture is then concentrated by evaporation on a rotary evaporator at 70° C. under reduced pressure and the residue is dried overnight under a high vacuum. N-trimethylsilyl-3-deoxy-3,3-dimethylsaccharin is obtained in virtually quantitative yield as a white powder which melts at 144°-146° C.

EXAMPLE 2

(−)-N-Trimethylsilylcamphor sultam

The procedure of Example 1 is repeated, using (−)-camphor sultam (ex Aldrich) instead of saccharin, to give pale beige crystals of (−)-N-trimethylsilylcamphor sultam in virtually quantitative yield. Melting point: 63°-73° C.

EXAMPLE 3

N-Fluoro-3-deoxy-3,3-dimethylsaccharin

Excluding air and moisture, 40 mmol of the compound of Example 1 in a mixture of 250 ml of $CHCl_3/CFCl_3$ (3:2) is reacted for 3 hours at $-40°$ C. with a mixture of 10% by volume of fluorine in nitrogen. After blanketing with nitrogen at room temperature, the reaction mixture is concentrated on a rotary evaporator under reduced pressure and the residue is recrystallised from ether/pentane, affording white crystal needles of N-fluoro-3-deoxy-3,3-dimethylsaccharin in virtually quantitative yield. Melting point: 114°-116° C.

EXAMPLE 4

(−)-N-Fluorocamphor sultam

The procedure described in Example 3 is repeated using the compound of Example 2, but additionally chromatographing the residue over silica gel before effecting recrystallisation from $CH_2Cl_2$. Based on the batch, white crystals of (−)-N-fluorocamphor sultam are obtained in virtually quantitative yield. Melting point: 104° C.; optical rotation $[\alpha]_D^{20} = 10.6°$ (C=0.7 in $CHCl_3$).

EXAMPLE 5

N-Fluoro-3-deoxy-3,3-dimethylsaccharin

Excluding air and moisture, 25 mmol of 3-deoxy-3,3-dimethylsaccharin in a mixture of 200 ml of $CHCl_3/CFCl_3$ (1:1) are reacted for 20 minutes at $-40°$ C. with a mixture of 10% by volume of fluorine in nitrogen and in the presence of NaF. Working up is as described in Example 3. Yield: 4.0 g (74% of theory) of N-fluoro-3-deoxy-3,3-dimethylsaccharin with a melting point of 114°-116° C.

EXAMPLE 6

(+)-N-Fluoro-3-tert-butyl-3-deoxy-3-methylsaccharin (a) 1,2-Benzisothiazole-3-tert-butyl-1,1-dioxide The reaction of 1,2-benzisothiazole-3-chloro-1,1-dioxide with tert-butyl magnesium chloride in absolute tetrahydrofuran (THF) at room temperature gives yellow crystals of 1,2-benzisothiazole-3-tert-butyl-1,1-dioxide which melt at 105°-110° C. (recrystallisation from diethyl ether).

(b) (±)-3-tert-Butyl-3-deoxy-3-methylsaccharin

The reaction of compound (a) with methyllithium in absolute THF at $-78°$ C. gives colourless crystals of (±)-3-tert-butyl-3-deoxy-3-methylsaccharin which melt at 170°-172° C. (recrystallisation from toluene).

(c) (±)-N-Fluoro-3-tert-butyl-3-deoxy-3-methylsaccharin

The process described in Example 5 is repeated, using the compound of (b). Working up is as described in (b), except that the oily product is chromatographed over silica gel (elution with a 5:1 mixture of hexane/ethyl acetate). Yield: 83% of a colourless oil. $^1$H-NMR (300 MHz, $CDCl_3$): 1.14 ppm (d,9H), 1.65 ppm (d,3H), 7.55-7.80 (m,4H).

EXAMPLE 7

(±)-N-Fluoro-2-methylcamphor sultam (a) (−)-2-Methylcamphor sultam

The (−)-camphor sulfonimide described by Oppolzer et al. in Tetrahedron 42, 4035-4043 (1986) is methylated at room temperature with methyl magnesium iodide in the presence of 1 equivalent of copper(I) chloride in diethyl ether, affording colourless crystals of homogeneous (−)-2-methylcamphor sultam which melt at 240°-243° C. and have an optical rotation $[\alpha]_D^{20} = -36.1°$ C. (C=1.00 in $CHCl_3$).

(b) (+)-N-Fluoro-2-methylcamphor sultam

The procedure of Example 5 is repeated, using the compound of (a). After filtration and concentration on a rotary evaporator, the residue is recrystallised from $CH_2Cl_2$, affording colourless crystals in 80% yield which melt at 151°-154° C. and have an opticial rotation $[\alpha]_D^{20} = +10.27$ (C=0.74 in $CHCl_3$).

(B) USE EXAMPLES

EXAMPLE 8

Preparation of E-1-fluoro-1-octene

To a solution of 4 mmol of E-1-iodo-1-octene in 30 ml of tetrahydrofuran are added 5.7 ml (8 mmol) of tert-butyllithium (1.4M solution in pentane) at −78° C. over 30 minutes and, after 30 minutes, a solution of 6 mmol of N-fluoro-3-deoxy-3,3-dimethylsaccharin (Example 3) in 6 ml of tetrahydrofuran. The reaction mixture is stirred overnight, and subsequently volatile products together with the solvent are stripped off under a high vacuum. The residue is condensed in a vessel cooled with liquid nitrogen and the residue is subjected to fractional distillation, to give a mixture of 1-octane and E-1-fluoro-1-octene which boils at 80° C.

EXAMPLE 9

Preparation of E- and Z-1-fluoro-4-thexyldimethyldilyloxy-1-butene (a) Thexyldimethylsilyloxy-1-butyne To a solution of 0.37 mol of 1,8-diazabicyclo[5.4.0]undec-7-ene and 0.36 mol of thexyldimethylchlorosilane in 300 ml of methylene chloride is added 0.338 mol of 3-butyn-1-ol over 10 minutes. After 15 minutes, the mixture is washed with water, 0.1N HCl and sodium bicarbonate solution, dried over $Na_2SO_4$ and filtered. The filtrate is concentrated by evaporation and distillation of the residue gives the desired product with a boiling point of 86°-89° C./20 mbar.

(b) 4-Thexyldimethylsilyloxy-1-tributylstannyl-1-butene (E/Z=4:1)

A mixture of 10.6 g (0.05 mol) of the alkyne (a) and 14.6 ml (0.055 mol) of tributyltin hydride is irradiated overnight at −10° C. to 0° C. with a 200 W electric lamp and the product is thereafter isolated by distillation. Yield: 23 g of compound (b) with a boiling point of 126°-145° C./0.01 mbar.

(c) E- and Z-1-Fluoro-4-thexyldimethylsilyloxy-1-butene

To a solution of 3 mmol of (b) in 22 ml of a solvent system consisting of THF/diethyl ether/pentane (4:1:1) are added, at −70° C., 2.25 ml (3.6 mmol) of butyllithium (1.6M in hexane), and the mixture is left for 45 minutes at this temperature. After cooling to −120° C., a solution of 3 mmol of N-fluoro-3-deoxy-3,3-dimethylsaccharin (Example 3) in 3 ml of THF is added. After 1 hour at −120° C. to −110° C., the reaction mixture is warmed to room temperature, diluted with water and extracted with hexane. The extract is dried and concentrated by evaporation, and the residue is subjected to flash chromatography over silica gel (elution with cyclohexane). The title compound is obtained as a mixture of the E and Z isomers (4:1).

$^1$H-NMR (300 MHz, $CDCl_3$); E-isomer: 6.52 (C—1H); 5.35 (C—2H); 2.33 (C—3H);
3.62 (C—4H). Z-isomer: 6.47 (C—1H); 4.80 (C—2H); 2.09 (C—3H); 3.62 (C—4H).

EXAMPLE 10

Preparation of (+)-1-fluoro-1-carbethoxycyclopentan-2-one

To a suspension of 1.56 mmol of sodium hydride in 5 ml of tetrahydrofuran are added, at 0° C., 1.3 mmol of 1-carboethoxycyclopentan-2-one and the mixture is stirred for 1 hour at 0° C. Then a solution of 1.4 mmol of (−)-N-fluorocamphor sultam (Example 4) is added dropwise, and stirring is continued for 3 hours at 0° C. The reaction mixture is then poured into 50 ml of 1M oxalic acid and extracted with diethyl ether. The organic phases are washed with 10% $NaHCO_3$ solution and with a saturated solution of NaCl. The resultant mixture is purified over a column of silica gel, affording (+)-1-fluoro-1-carboethoxycyclopentan-2-one in high purity (ee=70%).

$^1$H-NMR: (300 MHz, $CDCl_3$): 1.32 ppm (t, 3 H,), 2.16 ppm (m, 2 H); 2.31 ppm (m, 1 H); 2.50 ppm (t, 2 H); 2.55 ppm (m, 1 H); 4.30 ppm (q, 2 H).

EXAMPLE 11

Preparation of (+)-1-fluoro-1-carbethoxycyclopentan-2-one

In accordance with the procedure of Example 10, but using potassium hydride in the system toluene/THF (2:1), the enolate of 1-carboethoxycyclopentan-2-one is formed and fluorinated with (+)-N-fluoro-2-methylcamphor sultam (Example 7). Purity of the enantiomer in the desired product: ee=ca. 5%.

EXAMPLE 12

Preparation of ethyl 2-fluoro-2-methyl acetate

In accordance with Example 10, but using lithium hydride in diethyl ether, the enolate of ethyl 2-methyl acetate is prepared and fluorinated at room temperature with (−)-N-fluorocamphor sultam (Example 4). Purity of the enantiomer in the desired product: ee=ca. 10%.

EXAMPLE 13

Preparation of ethyl 2-fluoro-2-phenylpropionate

In accordance with Example 10, but using lithium dimethylamide in THF at 78° C., the enolate of ethyl 2-phenylpropionate is prepared and fluorinated at room temperature with (−)-N-fluorocamphor sultam (Example 4). Purity of the enantiomer in the desired product: ee=ca. 35%.

EXAMPLE 14

Preparation of ethyl 2-fluoro-2-phenylpropionate

In accordance with Example 13, the corresponding enolate is formed and fluorinated at room temperature with (+)-N-2-methylcamphor sultam (Example 7). Purity of the enantiomer in the desired product: ee=ca. 10%.

EXAMPLE 15

Preparation of 2-fluoro-2-methyl-1-oxo-1,2,3,4-tetrahydronaphthalene

In accordance with Example 13, the enolate of 2-methyl-1-oxo-1,2,3,4-tetrahydronaphthalene is prepared and fluorinated at room temperature with (−)-N-fluorocamphor sultam (Example 4). Purity of the enantiomer in the desired product: ee=ca. 35%.

EXAMPLE 16

Preparation of methyl (±)-2-fluoro-2-phenylpropionate

In accordance with Example 14, the corresponding enolate is prepared and fluorinated at room temperature with N-fluoro-3-deoxy-3,3-dimethylsaccharin. Yield: 70%

$^1$H-NMR (300 MHz, CDCl$_3$): 1.91 (d, 3H), 3.74 (s, 3H), 7.30–7.53 (m, 5H).

EXAMPLE 17

Preparation of methyl (±)-2-fluoro-2-phenylpropionate

In accordance with Example 14, the corresponding enolate is prepared and fluorinated at room temperature with (±)-N-fluoro-3-tert-butyl-3-deoxy-3-methylsaccharin (Example 6). Yield: 43%.

What is claimed is:

1. A compound of formula I

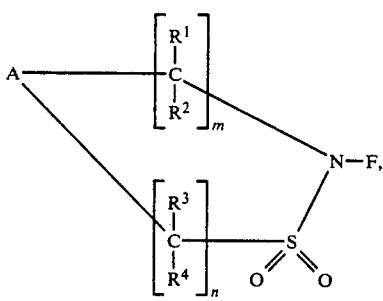

(I)

wherein $R^1$, $R^2$, $R^3$ and $R^4$ are each independently H, linear or branched $C_1$–$C_{18}$alkyl or $C_6$–$C_{10}$aryl, each unsubstituted, or alkyl is substituted by halogen, $C_6$–$C_{10}$aryl or $C_6$–$C_{10}$aryloxy, $C_1$–$C_6$alkoxy or secondary amino, and aryl is substituted by $C_1$–$C_{12}$alkyl, $C_1$–$C_{12}$haloalkyl or $C_1$–$C_{12}$alkoxy, halogen, phenyl, phenoxy or secondary amino, m and n are each independently of the other 0 or 1, and A is a divalent organic radical which, together with the ${(CR^1R^2)_m}$NF—SO$_2$(CR$^3$R$^4$)$_n$ group, forms a 5- to 8-membered ring, and the radical A is selected from the group consisting of (a) $C_1$–$C_6$alkylene, $C_2$–$C_6$alkenylene, $C_4$–$C_6$alkdienylene, $C_6$alktrienylene, $C_5$–$C_8$cycloalkylene, $C_5$–$C_8$cycloalkenylene, $C_5$–$C_8$cycloalkdienylene or $C_7$–$C_8$cycloalktrienylene, the cycloaliphatic radicals may be bridged with a ${(CR^5R^6)_x}$ group, wherein $R^5$ and $R^6$ are each independently of the other H or $C_1$–$C_4$alkyl and x is 1 or 2; and (b) $C_6$–$C_{14}$arylene; and the ring A is unsubstituted or substituted by one or more of $C_1$–$C_6$alkyl or $C_1$–$C_6$alkoxy, secondary amino, phenyl, phenoxy, Cl and Br, and the radical A, as cyclic radical, is also substituted by F.

2. A compound of formula I according to claim 1, wherein m and n are 1, or m is 0 and n is 1, or n is 0 and m is 1.

3. A compound of formula I according to claim 1, wherein A together with the ${(CR^1R^2)_m}$NF—SO$_2$(CR$^3$R$^4$)$_n$ group is a 6-membered ring and, preferably, a 5-membered ring.

4. A compound according to claim 3, wherein m is 0 and n is 1, or n is 0 and m is 1.

5. A compound of formula I according to claim 1, wherein m and n are 1 and A is unsubstituted or substituted alkylene of 1 or 2 carbon atoms.

6. A compound according to claim 1, wherein m is 0 and n is 1, or m is 1 and n is 0, and A is unsubstituted or substituted alkenylene of 2 to 3 carbon atoms, or cycloalkylene, cycloalkenylene or cycloalkdienylene, each of 5 or 6 carbon atoms, and the cyclic radicals may be bridged with a $(CR^5R^6)_x$ group, wherein $R^5$ and $R^6$ are each independently of the other $C_1$–$C_4$alkyl or H, and x is 1 or 2.

7. A compound according to claim 6, wherein the $(CR^5R^6)_x$ group is methylene, ethylidene, 1-1,- or 1,2-propylidene, ethylene or methylethylene.

8. A compound of formula I according to claim 1, wherein n is 0 and m is 1 or m is 0 and n is 1, and the radical A is unsubstituted or substituted 1,2-naphthylene or 1,2-phenylene.

9. A compound of formula I according to claim 1, wherein $R^1$, $R^2$, $R^3$ and $R^4$ are each independently H or unsubstituted or substituted $C_1$–$C_6$alkyl or phenyl.

10. A compound of formula I in the form of its racemate or individual stereoisomers, wherein the carbon atoms of the ${(CR^1R^2)}$ group and/or ${(CR^3R^4)}$ group are chiral, and/or the radical A contains at least one chiral carbon atom.

11. A compound of formula I according to claim 10, wherein the chiral carbon atoms are in α- or β-orientation to the NF group.

12. A compound of formula I according to claim 8, wherein m is 1 and n is 0, $R^1$ and $R^2$ are as defined in claim 1, and A is unsubstituted or substituted 1,2-phenylene.

13. A compound according to claim 12, wherein $R^1$ and $R^2$ are different radicals, in the form of its racemate or stereoisomer.

14. A compound according to claim 12, which is 3-deoxy-3,3-dimethyl-N-fluorosaccharin.

15. A compound of formula I according to claim 1, wherein m is 0 and n is 1, $R^3$ and $R^4$ are each H and A is unsubstituted or substituted $C_5$–$C_6$cycloalkylene which contains at least one chiral carbon atom and which can be bridged preferably with methylene, ethylidene, 1,1- or 2,2-propylidene or ethylene, in the form of the racemate or individual stereoisomers.

16. A compound according to claim 15, wherein A is cyclohexylene which is unsubstituted or substituted in α-position to the NF group by $C_1$–$C_4$alkyl or phenyl, and which can be bridged with methylene, ethylidene, 1,1- or 2,2-propylidene or ethylene.

17. A compound according to claim 15, which is N-fluorocamphor sultam of formula

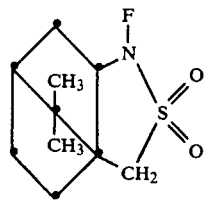

in the form of its racemate or of the individual stereoisomers.